US012580055B2

(12) United States Patent
Preuss-Dodhy

(10) Patent No.: US 12,580,055 B2
(45) Date of Patent: Mar. 17, 2026

(54) MEDICAL LABORATORY COMPUTER SYSTEM

(71) Applicant: Roche Diagnostics Operations, Inc., Indianapolis, IN (US)

(72) Inventor: Asad Preuss-Dodhy, Olching (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 180 days.

(21) Appl. No.: 18/463,834

(22) Filed: Sep. 8, 2023

(65) Prior Publication Data

US 2024/0096456 A1 Mar. 21, 2024

(30) Foreign Application Priority Data

Sep. 15, 2022 (EP) .................................... 22195990

(51) Int. Cl.
| | |
|---|---|
| *G16H 10/40* | (2018.01) |
| *G06F 21/60* | (2013.01) |
| *G16H 10/60* | (2018.01) |
| *H04L 9/40* | (2022.01) |

(52) U.S. Cl.
CPC .......... *G16H 10/40* (2018.01); *G06F 21/602* (2013.01); *G16H 10/60* (2018.01); *H04L 63/0421* (2013.01)

(58) Field of Classification Search
CPC ........ G16H 10/40; G16H 10/60; G16H 15/00; G16H 40/20; G06F 21/602; G06F 21/6254; G06F 21/6245; H04L 63/0421; H04L 67/12
See application file for complete search history.

(56) References Cited

U.S. PATENT DOCUMENTS

| | | | |
|---|---|---|---|
| 9,202,084 B2 | 12/2015 | Moore | |
| 10,417,451 B2 * | 9/2019 | Park | ...................... G06F 16/288 |
| 10,984,128 B1 | 4/2021 | Hoffer | |

(Continued)

OTHER PUBLICATIONS (IJACSA) International Journal of Advanced Computer Science and Applications, vol. 12, No. 9, 2021, pp. 757-762 (Year: 2021).*

(Continued)

*Primary Examiner* — Kambiz Abdi
*Assistant Examiner* — Sheryl G Patel
(74) *Attorney, Agent, or Firm* — Lee & Hayes, P.C.

(57) ABSTRACT

A healthcare computer system, the computer system comprising a communications module, a string generation module, a one-way function module and an anonymised data generation module. The communications module is configured to receive one or more healthcare data packets, each healthcare data packet including: data pertaining to one or more medical analytical tests performed on a sample; a sample identifier, identifying the sample; and a timestamp, indicating when the analytical test(s) was performed. The string generation module is configured to generate a string based on the sample identifier and the timestamp. The one-way function module is configured to apply a one-way function to the generated string to generate an anonymised sample identifier. The anonymised data generation module is configured to generate an anonymised healthcare data packet including the data pertaining to the one or more medical analytical tests and the anonymised sample identifier.

20 Claims, 6 Drawing Sheets

(56)     References Cited

U.S. PATENT DOCUMENTS

| | | | | |
|---|---|---|---|---|
| 11,080,423 | B1 * | 8/2021 | Kassam-Adams ..... | G16H 15/00 |
| 11,270,027 | B2 * | 3/2022 | Rosenberg ............ | G16H 10/60 |
| 11,907,397 | B2 * | 2/2024 | Raduchel ........... | G06F 21/6245 |
| 2015/0302148 | A1 * | 10/2015 | Fielder .................. | G16H 10/60 |
| | | | | 713/193 |
| 2016/0085915 | A1 * | 3/2016 | Seow ..................... | G16Z 99/00 |
| | | | | 705/3 |
| 2016/0306999 | A1 * | 10/2016 | Beinhauer .......... | G06F 21/6254 |

OTHER PUBLICATIONS

Anonymous, Data anonymisation—a key enabler for clnical data
sharing Workshop report, The MRCT Center of Brigham and
Women's Hospital and Harvard and European Medicines Agency,
2018, 32 pp., London.
European Search Report issued Feb. 28, 2023, in Application No.
22195990.1, 2 pp.

* cited by examiner

| Healthcare Data Packet | |
|---|---|
| Sample ID | 15438 |
| Timestamp | 01/09/2022 |
| Facility ID | 012 |
| Medical Analytical Test #1 | XXXXXX |
| Medical Analytical Test #2 | XXXXXX |
| ... | ... |
| Medical Analytical Test #n | XXXXXX |

Fig. 3A

| Anonymised Healthcare Data Packet | |
|---|---|
| Anonymised Sample ID | AF68 3410 9GW4 |
| Medical Analytical Test #1 | XXXXXX |
| Medical Analytical Test #2 | XXXXXX |
| ... | ... |
| Medical Analytical Test #n | XXXXXX |

Receive healthcare data packet(s)

S420

Generate string

S430

Apply one-way function to the string

S440

Generate anonymised healthcare data packet

S450

Transmit anonymised healthcare data packet

MEDICAL LABORATORY COMPUTER SYSTEM

CROSS-REFERENCE TO RELATED APPLICATIONS

This application claims priority to European Patent Application No. 22195990.1 filed Sep. 15, 2022, the disclosure of which is hereby incorporated by reference in its entirety.

FIELD OF THE DISCLOSURE

The present disclosure relates to secure healthcare data management systems and methods.

BACKGROUND

Medical laboratory equipment analysing a sample taken from a patient generates healthcare data from that analysis, as well as data relating to the equipment itself (for example consumable levels). The healthcare data generated from the analysis is typically packaged into a healthcare data packet, that healthcare data packet containing: data pertaining to one or more medical analytical test performed on the sample, a sample identifier (ID) and a timestamp. This packaging of healthcare data into packets is usually conducted within a laboratory information system (LIS), but could be performed in the laboratory instrument, in a middleware, or another device.

More than one form of analysis may be conducted on any given sample, resulting in data pertaining to plural medical analysis tests. Typically, the aim is to package the data pertaining to different medical analytical tests, but based on the same sample (e.g. using aliquots), into the same healthcare data packet. However, often not all of the data based on the same sample is put into the same healthcare data packet, meaning more than one healthcare data packet corresponding to a given sample ID may be generated.

A particular concern with medical data is that the sample ID, which is associated with the medical analytical test data generated from the analysis of that sample by the healthcare data packet, can be used to identify the patient from which that sample was obtained.

This concern is particularly acute where healthcare data packets need to be transmitted across a network, or more generally outside of a secure area of the LIMS, for use outside the medical laboratory that conducted the analysis on the sample. This is because the healthcare data packets are more vulnerable to interception during transmission outside the secure area of the LIS.

Moreover, with medical laboratory computer systems that associate IDs with data and/or samples, IDs are typically re-used on a regular basis (daily, weekly, monthly etc.), but there is also a concern regarding the likelihood of ID collision, i.e. the same ID being associated with data and/or samples that are not related to each other, potentially leading to erroneous analysis of that data.

The present disclosure has been devised in light of the above considerations.

SUMMARY

Accordingly, some embodiments of the disclosure provide a healthcare computer system, the computer system comprising:

a communications module, configured to receive one or more healthcare data packets, each healthcare data packet including:

data pertaining to one or more medical analytical tests performed on a sample;

a sample identifier, identifying the sample; and a timestamp;

a string generation module, configured to generate a string based on: the sample identifier and the timestamp;

a one-way function module, configured to apply a one-way function to the generated string to generate an anonymised sample identifier; and an anonymised data generation module, configured to generate an anonymised healthcare data packet including:

the data pertaining to the one or more medical analytical tests, and the anonymised sample identifier.

Such a system can ensure the privacy of patient data whilst also ensuring that the risk of anonymised sample ID collision is kept acceptably low.

The string generation module may generate the string directly from the sample identifier and the timestamp, or indirectly from the sample identifier and the timestamp. By indirectly, it may be meant that the sample identifier and the timestamp undergo one or more changes before being used by the string generation module. For example, the sample identifier and time stamp may first be provided, separately, to the one-way function module, which may be configured to apply a one-way function to each of the sample identifier and the timestamp separately. The resulting data can be combined by the string generation module, with this then being provided (again) to the one-way function as a composite string.

By one-way function, it may be meant an algorithm which takes an input and provides an output which is based on the input in a manner which is not reversable. That is, it is not possible take a given output and reverse engineer the input which provided that output.

The healthcare computer system may further comprise a random string generator. The random string generator may be configured to generate a random string and the string generation module may then be configured to generate the string further based on the random string. Incorporating a random string into the string can further reduce the risk of anonymised sample ID collision, and further enhance security by reducing the applicability of rainbow table attacks.

The healthcare computer system may be a medical laboratory computer system.

The communications module may be configured to receive plural healthcare data packets. The plural healthcare data packets may arrive within a single file, for example a single XML file.

The timestamp may indicate when the analytical test was performed. The timestamp may indicate when the healthcare data packet was transferred to or received by the communications module. The timestamp may indicate when a request was made for one or more medical analytical tests to be performed on the sample.

The timestamp may be indicative of a counting period. The counting period may define a period of time over which (different) sample identifiers are generated and at the end of which the counting period sample identifiers begin to be reused. For example, a counting period may be 24 hours or multiple days, during which sample identifiers are sequentially generated (e.g. 0001, 0002, 0003, etc.). At the end of the counting period, the sample identifiers may be refreshed, and duplicate sample identifiers (relative to the previous counting period) are generated once more. Where the timestamp is indicative of a counting period, it may be indicative of a beginning of the counting period or of an end of the counting period. In an example where the counting period is a day (therefore changing at midnight), the timestamp may be indicative of the beginning of this period (e.g. [DATE] 0000) or the end of this period ([DATE]2359) or the date itself ([DATE]), where [DATE] is the present date.

Where the timestamp is indicative of a counting period during which sample identifiers are generated, and the healthcare computer system includes a random string generator, the random string generator may be configured to generate a single random string to be used with all healthcare data packets received by the communications module within the counting period. In this way, where two or more healthcare data packets are received with a same sample identifier, the same generated random string will be used by the string generation module, and so the same anonymised sample identifier will be generated for the two or more healthcare data packets.

The healthcare computer system having a random string generator may further be configured such that:

the communications module is configured to receive a first healthcare data packet of the one or more healthcare data packets and a second healthcare data packet of the one or more healthcare data packets, wherein the first healthcare data packet and the second healthcare data packet include a same sample identifier and a same timestamp;

the random string generator is configured to generate a shared random string for the first and second healthcare data packets;

the one-way function module is configured to generate a same anonymised sample identifier for each of the first and second healthcare data packets; and the anonymised data generation module is configured to generate a first anonymised healthcare data packet and a second anonymised healthcare data packet, the first and second anonymised healthcare data packets having the same anonymised sample identifier.

Such a system can allow the first and second healthcare data packets to be associated with each other even after those healthcare data packets have been anonymised.

The string generation module may be configured to concatenate the sample identifier and the timestamp.

The system may receive a plurality of healthcare data packets. This plurality of healthcare data packets may be received sequentially or in a batch of healthcare data packets. Where the plurality of healthcare data packets is a batch of healthcare data packets, and the system includes a random string generator, a same random string may be used for each of the individual packets within the batch or a different random string may be generated for each packet within the batch (unless they share a same sample identifier, in which case the same should be use for each with the same sample identifier).

Where the healthcare data packet further includes a facility identifier identifying the facility in which the one or more analytical tests were performed, the string generation module of the healthcare computer system may be configured to generate the string further based on the facility identifier. Such a system can further reduce the risk of anonymised sample ID collision where two facilities (perhaps owned by a single operator) generate sample identifiers according to a same scheme.

Where the healthcare data packet further includes a lab operator identifier identifying the lab operator operating the laboratory in which the one or more analytical tests were performed, the string generation module of the healthcare computer system may be configured to generate the string further based on the lab operator identifier. Such a system can further reduce the risk of anonymised sample ID collision where two laboratories (owned by different operators) generate sample identifiers according to a same scheme.

The one-way function module may be configured to generate the anonymised sample ID from the string by applying a cryptographic hash function to the string. Advantageously, a cryptographic hash function is practically infeasible to reverse, reducing the risk of the anonymised sample ID being usable to identify the original sample ID, and thus the patient from which the sample was obtained. Thus, the system can ensure the privacy of patient data. Moreover, cryptographic hash functions very infrequently generate the same anonymous sample ID from differing strings, further reducing the risk of anonymous sample ID collision.

The timestamp may indicate the date on which the analytical test was performed. Preferably it is no more granular than the date on which the analytical test was performed. Such timestamp data reduces the likelihood of data pertaining to different medical analytical tests performed on the same sample being included in separate healthcare data packets, thereby reducing the number of healthcare data packets the system needs to process.

The communications module of the healthcare computer system may be further configured to transmit the anonymised healthcare data packet to a server for inclusion in an anonymised healthcare dataset. The anonymised healthcare data set can be used, for example, for: (a) benchmarking, e.g. to optimise the performance of laboratories and other healthcare organisations relative to a group of peers, or to analyze regional testing behaviours; (b) providing insights to help forecast future and potential healthcare threats and trends, e.g., anticipation and preparation for potential disease outbreaks, forecasting regional testing behaviour; (c) improving and managing customer support and supply processes, e.g., supply production forecasting; (d) providing and improving manufacturer products and services in the field of healthcare, e.g., training AI solutions or providing reference range values for instruments; (e) supporting regulatory approval of products or other regulatory requirements; (f) other scientific and/or statistical purposes in the field of healthcare, e.g., to improve diagnostic pathways for patients, to identify unmet medical needs or gaps; and/or (g) improving predictive maintenance of laboratory instruments.

Where the communications module is configured to transmit plural anonymised healthcare data packets to a server, the communications module may group a plurality of anonymised healthcare data packets over a time period, and transmit them in batches to the server. Where a plurality of anonymised healthcare data packets are grouped together, this may be in the form of: a table, where each entry is a given anonymised healthcare data packet; or as a single XML file containing plural healthcare data packets.

Within the healthcare computer system, the communications module and anonymised data generation module may be within a first security area of a network, and the communications module may be configured to transmit the anonymised healthcare data packet outside of the first security area.

The healthcare data packet(s) may be provided as XML (extensible mark-up language) files. The anonymised healthcare data packets may also be provided as XML files. The healthcare data packets may be received periodically by the system, for example once every 24 hours.

Typically, the data pertaining to one or more medical analytical tests performed on the sample may contain one or more or all of the following categories of data: (i) medical data, for example measurements performed on the sample; (ii) technical data, for example quality control data generating by the instrument; and (iii) consumption data, for example information about the consumables used in the instrument. The data pertaining to one or more medical analytical tests performed on the sample may include in-vitro diagnostic test results. It may include direct analytical test results or measurements, patient metadata pertaining to the test (for example, an age of the patient, BMI, sex, etc.), and/or machine metadata (e.g. serial number of the instrument, position of the sample in the tray, the lot number of reagent used, operating conditions, for example temperature or reagent level).

The data pertaining to one or more medical analytical tests performed on the sample may include medical test results.

The healthcare computer system may be, or form a part of, a laboratory middleware. The laboratory middleware may be the entity assigning sample identifiers. The healthcare computer system may be, or may form a part of, an instrument computer system. The instrument computer system may include one or more analytical instruments. Where the healthcare computer system is provided as or as a part of an instrument computer system, the communications module may be configured to receive the healthcare data packet from another part of the instrument computer system. The healthcare computer system may be a component connected to a laboratory middleware and/or an instrument computer system.

Some embodiments of the disclosure provide a computer-implemented method of generating anonymised healthcare data, comprising steps of:
  receiving one or more healthcare data packets, each healthcare data packet including:
    data pertaining to one or more medical analytical tests performed on a sample;
    a sample identifier, identifying the sample; and
    a timestamp;
  generating a string, based on: the sample identifier and the timestamp,
  applying a one-way function to the string to generate an anonymised sample identifier, and
  generating an anonymised healthcare data packet, said anonymised healthcare data packet including:
    the data pertaining to one or more medical analytical tests, and
    the anonymised sample identifier.

Such a method can ensure the privacy of patient data whilst also ensuring that the risk of anonymised sample ID collision is kept acceptably low.

The healthcare data packets received in the method may originate from an in-vitro diagnostics laboratory.

The method may include anyone, or any combination insofar as they are compatible, of the optional features set out with reference to the first aspect.

In a third aspect, embodiments of the disclosure provide a computer, the computer including: one or more processors, and memory, wherein the memory contains machine executable instructions which, when executed on the one or more processors, cause the processors to perform the computer-implemented method according to the second aspect, including any one or an combination insofar as they are compatible of the optional features set out with reference thereto.

In a fourth aspect, embodiments of the disclosure provide a computer or computer network, the computer or computer network including
  a communications module, configured to receive one or more healthcare data packets, each healthcare data packet including:
    data pertaining to one or more medical analytical tests performed on a sample;
    a sample identifier, identifying the sample; and
    a timestamp;
  a string generation module, configured to generate a string based on: the sample identifier and the time stamp;
  a one-way function module, configured to apply a one-way function to the generated string to generate an anonymised sample identifier; and
  an anonymised data generation module, configured to generate an anonymised healthcare data packet including:
    the data pertaining to one or more medical analytical tests, and
    the anonymised sample identifier.

Such a computer can ensure the privacy of patient data whilst also ensuring that the risk of anonymised sample ID collision is kept acceptably low.

The computer may have any one, or any combination insofar as they are compatible of the optional features as set out with reference to the first aspect.

In a fifth aspect, embodiments of the disclosure provide a non-transitory computer-readable storage medium, containing machine executable instructions which, when executed on one or more processors, cause the processor(s) to perform the computer-implemented method according to the second aspect.

In a sixth aspect, embodiments of the disclosure provide a computer or computer network containing a computer-readable storage medium and one or more processors, wherein the computer-readable storage medium contains machine executable instructions which, when executed on one or more processors, cause the processor(s) to perform the computer-implemented method according to the second aspect.

The disclosure includes the combination of the aspects and preferred features described, except where such a combination is clearly impermissible or expressly avoided.

BRIEF DESCRIPTION OF THE DRAWINGS

Embodiments of the disclosure will now be described by way of examples with reference to the accompanying figures in which:

FIG. 3A is an example of the information contained in a healthcare data packet;

FIG. 3B is an example of the information contained in an anonymised healthcare data packet;

DETAILED DESCRIPTION

Aspects and embodiments of the present disclosure will now be discussed with reference to the accompanying figures. Further aspects and embodiments will be apparent to those skilled in the art.

Figure 1:
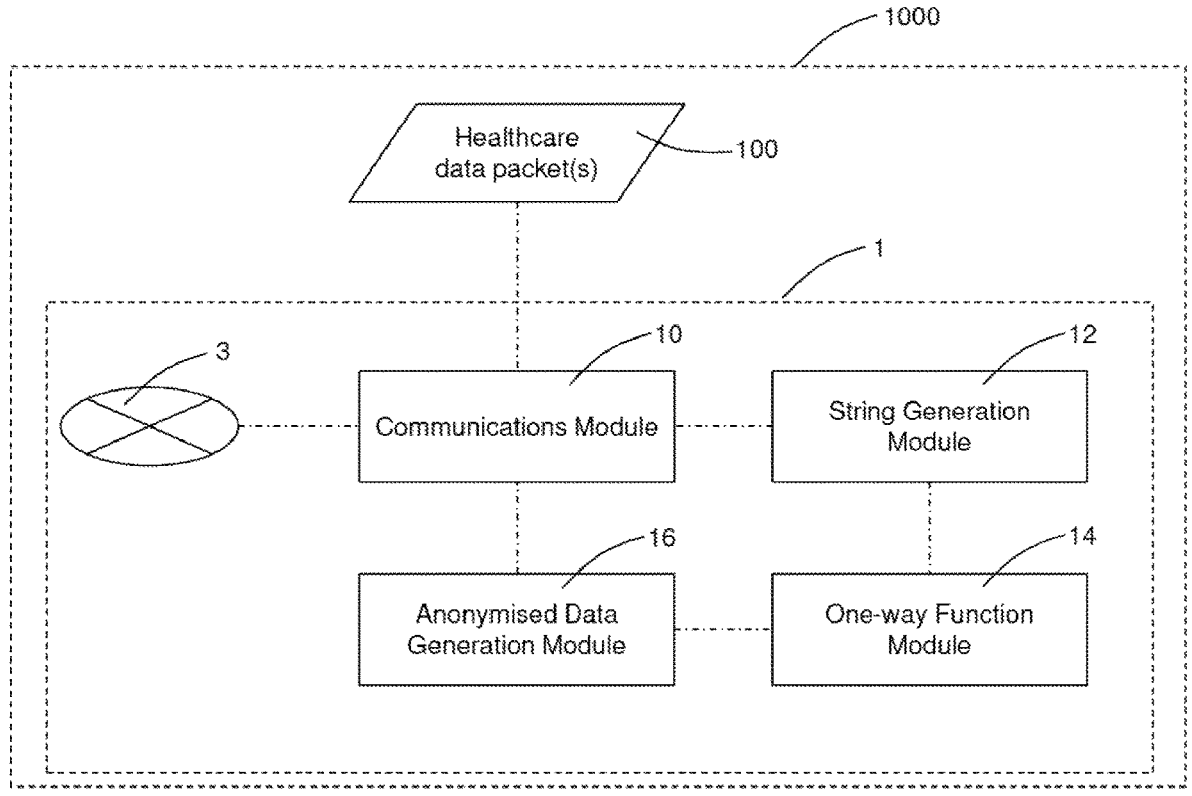
FIG. 1 is a schematic of a healthcare computer system.

FIG. 1 is a schematic of a healthcare computer system 1 and the healthcare data packet(s) 100 the healthcare computer system 1 receives. The healthcare computer system 1 in this example forms part of a laboratory information system (LIS) 1000, another sub-system of which generates the healthcare data packets 100. In other examples the healthcare computer system 1 may be a standalone system, for example one or more standalone computers. The LIS 1000 may form part of a larger healthcare data management system, other parts of which the healthcare computer system 1 is connected to via a network. The healthcare computer system 1 receives one or more healthcare data packets 100 generated within the LIS 1000, the healthcare data packets 100 containing data pertaining to medical analytical tests obtained from one or more medical analytical tests performed on a sample from a patient, the medical analytical tests being performed using laboratory instruments.

The laboratory instruments may be, for example, pre-analytics instruments, analysers, or post-analytic instruments; one or more of the laboratory instruments may be cobas (RTM) 6000 analysers configured to perform measurements of proteins, enzymes, substrates and electrolytes, direct antiglobulin tests, and therapeutic drug monitoring. The medical laboratory providing the medical analytical test data for the healthcare data packet 100 may be an in-vitro diagnostics laboratory, for example in a hospital laboratory. Each healthcare data packet 100 includes: data pertaining to one or more medical analytical tests performed on a sample; a sample ID, identifying the sample; and a timestamp, indicating when the analytical test(s) was performed or being indicative of a counting period of the type discussed above. Where multiple medical analytical tests are performed on a sample, it is preferable that the LIS 1000 packages the data pertaining to different medical analytical tests performed on the same sample into the same healthcare data packet 100, hence the healthcare data packet 100 may include data pertaining to more than one medical analytical test performed on the same sample. The sample ID allows identification of the sample and could be used to identify the patient that the sample was obtained from. Sample IDs are typically re-used on a daily basis i.e. the sample corresponding to sample ID 1 on Jan. 9, 2022 is not necessarily the same sample corresponding to sample ID 1 on Feb. 9, 2022. Therefore, a timestamp is also included in each healthcare data packet 100, the timestamp indicating when the medical analytical test(s) was performed or the counting period as discussed above. The combination of the sample ID and timestamp allows the risk of ID collision (i.e. two samples being conflated with each other because of matching sample IDs) to be reduced. The timestamp, when indicative of when a medical analytical test was performed, may be no more precise than the date on which the medical analytical test(s) was performed. This is because the IDs are typically only reused each day (for example, where the counting period is a 24 hour period), meaning including more granular detail does not further reduce collision risk, and because only including the date allows the LIS 1000 to package more data pertaining to different medical analytical tests on the same sample into the same healthcare data packet 100, because a timestamp only corresponding to a date provides a wider window of time over which analytical tests to be included in the healthcare data packet could have been performed. An example of the information contained in a healthcare data packet 100 is provided by FIG. 3A. In FIG. 3A, the healthcare data packet 100 further includes a facility ID (012), identifying the facility in which the one or more medical analytical tests were performed. Including the facility ID in the healthcare data packet 100 can further reduce the risk of ID collision.

Anonymising the data contained within the healthcare data packets 100 by providing anonymised healthcare data packets results in it not being possible, or at least not practically feasible, to identify the patient the sample was obtained from. However, in anonymising the healthcare data packets, it is very important to reduce the likelihood of ID collision between two anonymised sample IDs contained within two anonymised healthcare data packets, because this could lead to the two anonymised healthcare data packets erroneously being taken to relate to the same sample.

The present healthcare computer system 1 is configured to generate anonymised healthcare data packets in a manner by which the risk of ID collision is kept acceptably low, whilst still ensuring the privacy of patient data.

The generation of anonymised healthcare data packets by the healthcare computer system 1 is described below with reference to the schematic in FIG. 1 and the flowchart in FIG. 4, the flowchart corresponding to the steps of a computer-implemented method of generating anonymised healthcare data.

The healthcare computer system 1 includes a communications module 10 (for example an I/O interface, or network interface), a string generation module 12, a one-way function module 14 and an anonymised data generation module 16. The modules of the system 1 are configured to be in communications with each other, as illustrated by the dash-dot lines in FIG. 1, such that data can be passed between the modules. The modules are implementable as software packages running on one or more computers. They may be connected to each other either by virtue of running on the same computer (physical or virtual) or may be connected via a network when located on distinct computers. The healthcare computer system 1 forms part of the broader LIS 1000 that handles the information coming into, being generated by, and leaving, the medical laboratory.

The communications module 10 is configured to receive one or more healthcare data packets 100 generated within the LIS 1000 (step S410), each healthcare data packet 100 including data pertaining to one or more medical analytical tests performed on a sample, a sample ID, and a timestamp. The healthcare data packet 100 may further include a facility ID.

Each sample ID, timestamp and facility ID (if present) are extracted from the respective healthcare data packet 100 and passed to the string generation module 12. The string generation module 12 generates a string based, directly or indirectly, on the sample ID, timestamp and facility ID (if present) (step S420). The string may be a concatenation of the sample ID and timestamp, for example, or the string generation module 12 may conduct more complex processing of the sample ID and timestamp to generate the string.

Having generated the string, it is passed from the string generation module 12 to the one-way function module 14. The one-way function module 14 is configured to apply a one-way function to the generated string to generate an anonymised sample ID (step S430). The one-way function provides the resulting ID with anonymity because whilst the one-way function is computationally cheap to apply, it is practically infeasible to invert such as to be able to convert the anonymised sample ID back to the string it was generated from. Typically, the one-way function is some form of cryptographic hash function (CHF), for example, one or more of the following CHFs can be used: Whirlpool, SHA-2, SHA-3, BLAKE2, BLAKE3, preferably one of SHA-2 or SHA-3. Cryptographic hash functions are practically infeasible to invert, reducing the risk of the anonymised sample ID being used to backtrack to the original sample ID, and thus the patient. Moreover, cryptographic hash functions typically have very good collision resistance (i.e. there are few pairs of different strings $S_1$, $S_2$, where hash $(S_1)$=hash $(S_2)$).

Once an anonymised sample ID is generated, it is provided from the one-way function module 14 to the anonymised data generation module 16. Using the anonymised sample ID and the medical analytical test data, which can be obtained from the communications module 10, the anonymised data generation module 16 generates an anonymised healthcare data packet including the medical analytical test data and the corresponding anonymised sample ID (step S440). An example of the information contained in an anonymised healthcare data packet is provided by FIG. 3B. The anonymised healthcare data packet in FIG. 3B does not contain the sample ID, the timestamp or the facility ID contained in the healthcare data packet in FIG. 3A.

By the healthcare computer system 1 generating an anonymised healthcare data packet, the medical analytical test data contained within that anonymised healthcare data packet can be shared outside the LIS 1000 with a low risk that the anonymised sample ID contained within the anonymised healthcare data packet could be used to identify the patient the sample originated from. Accordingly, the anonymised healthcare data packet may be provided to the communications module 10 and the communications module can transmit the anonymised healthcare data packet outside the LIS 1000 via the network using a network modem 3 or the like (step S450).

Figure 2:
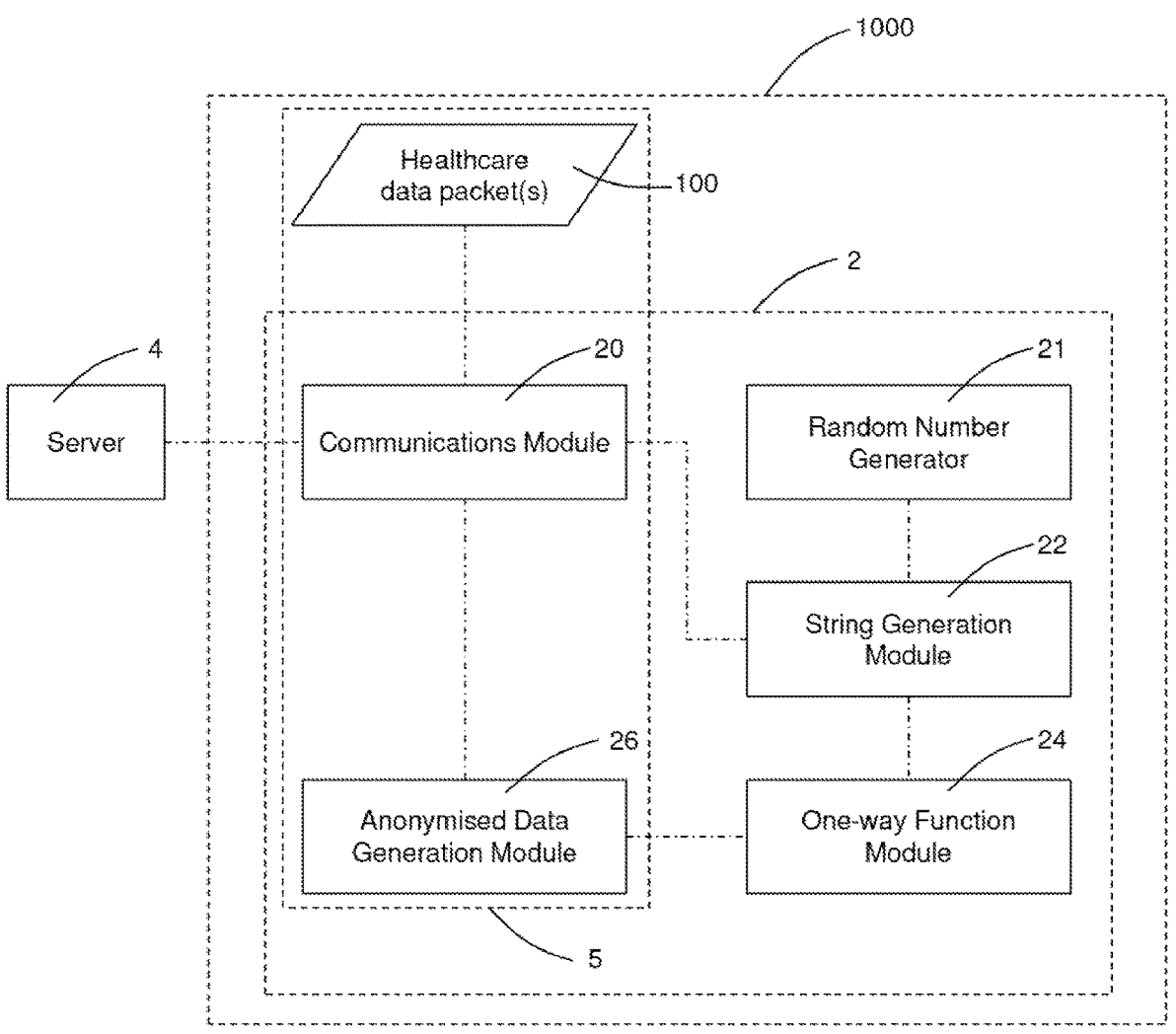
FIG. 2 is a schematic of a variant of the healthcare computer system in FIG. 1.

FIG. 2 illustrates a schematic of a variant of the healthcare computer system of FIG. 1. The healthcare computer system 2 illustrated in FIG. 2 includes a communications module 20, a random string generator 21, a string generation module 22, a one-way function module 24 and an anonymised data generation module 26. The random string generator may be configured to generate random strings of a fixed length. The random string generator may generate random strings which include symbols and/or alphanumeric characters. In one example, the random string generator is a random number generator configured to generate random numbers.

The communications module 20, one-way function module 24 and anonymised data generation module 26 are substantially the same as the equivalent modules discussed in relation to FIG. 1. The differences between the healthcare computer system 2 of FIG. 2 and that of FIG. 1 primarily relate to the random string generator 21 and string generation module 22. These differences are discussed below with reference to FIG. 5, which is a flowchart corresponding to the steps of a computer-implemented method of generating anonymised healthcare data.

The random string generator 21 generates a random string (step S515) to associate with each healthcare data packet 100 received by the communications module 20. The random string may be generated in parallel with the receipt of a healthcare data packet by the communications module 20

Figure 5:
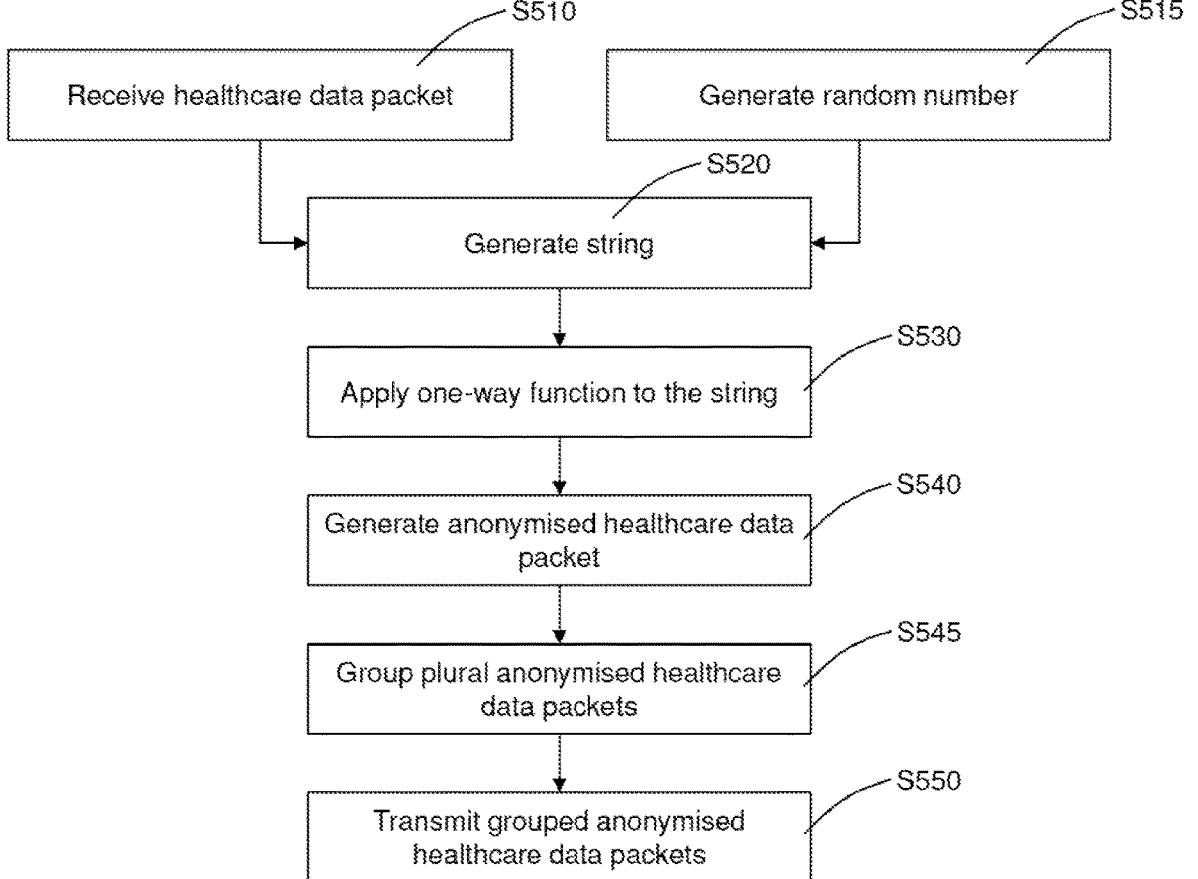
FIG. 5 is a flowchart corresponding to the steps of a computer-implemented method of generating anonymised healthcare data.

(as illustrated in FIG. 5), or may be generated in series with the receipt of that packet (i.e. before or after the healthcare data packet is received). The sample ID and timestamp, and optionally the facility ID (if present), of the healthcare data packet 100 are provided to the string generation unit 22 by the communications unit 10, and the corresponding random string is also provided to the string generation unit 22.

The string generation unit 22 is then configured to generate the string based on the sample ID, the timestamp, the random string and optionally the facility ID (step S520). As described above in relation to the string generation unit 12 of FIG. 1, the string generation unit 22 may concatenate the sample ID, timestamp and random string, or may conduct more complex processing of the inputs to the string generation unit 22 in order to generate the string.

Having generated the string, the healthcare computer system 2 proceeds to generate the anonymised healthcare data packet (steps S530 and S540) in substantially the same way as discussed above in relation to FIGS. 1 and 4 (steps S430 and S440).

The schematic in FIG. 2 also differs from that in FIG. 1 by the communications module 20 is optionally connected to a server 4 of the healthcare data management system located outside the LIS 1000 via the network (although the module 10 in FIG. 1 can equally be connected to server 4, and communicate in the manner discussed below). The communications module 20 can transmit the anonymised healthcare data packet to the server 4 (step S550), where it is stored as part of an anonymised healthcare dataset for use for other purposes.

The flowchart in FIG. 5 provides further detail on the step of transmitting the anonymised healthcare data packet. In FIG. 4, the transmission step S450 may involve simply transmitting each anonymised healthcare data packet as soon as, or soon after, it is generated by the anonymous data generation module 16. However, the approach of FIG. 5 is for the communications module 26 to group plural anonymised healthcare data packets over a time period (step S545) and subsequently transmit the grouped anonymised healthcare data packets to the server 4 (or elsewhere) in batches (step S550). The time period over which the communications module may group the plural anonymised healthcare data packets may be a 24 hour period, a 12 hour period, or a 6 hour period, preferably a 24 hour period.

FIG. 2 also illustrates that the communications module 20 and the anonymised data generation module 26 are contained within a first security area 5 of the network and that the communications module is configured to transmit the anonymised healthcare data packets outside of the first security area 5. The first security area 5 may have more stringent network security protocols than the remainder of the network, since it is this first security area that contains data where a given sample ID is directly associated with its respective medical analytical test data, whilst in the rest of the network the sample ID is not present together with its respective medical analytical test data: either the analytical test data is not present with the sample ID (for example, in the string generation module 22 and one-way function module 24), or it is only the anonymised sample ID that is present (for example, in the server 4).

Figure 6:
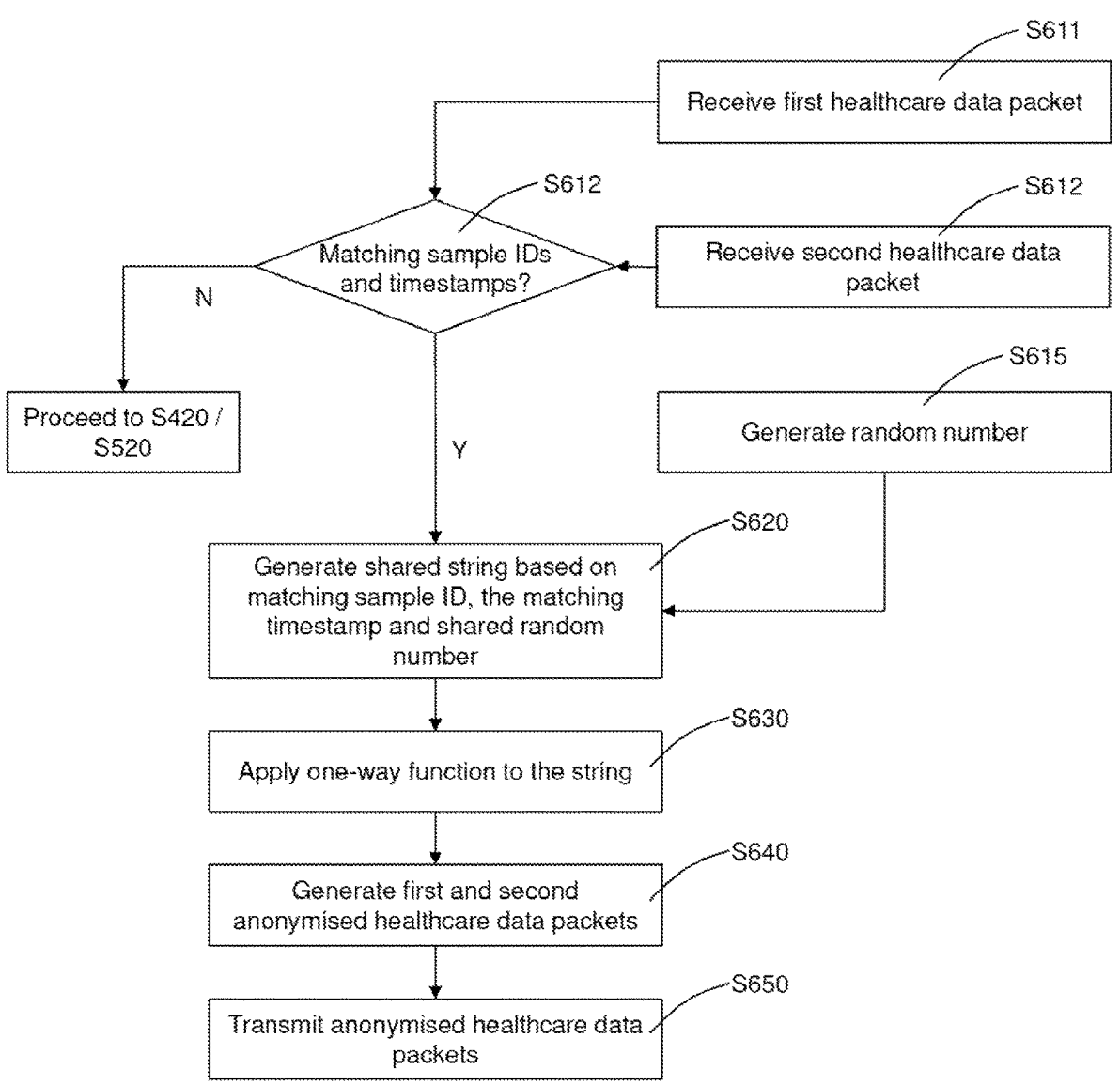
FIG. 6 is a flowchart corresponding to the steps of a computer-implemented method of generating anonymised healthcare data.

FIG. 6 is a flowchart corresponding to the steps of a computer-implemented method of generating anonymised healthcare data that is a variant of the computer-implemented method represented by FIG. 5. The method of FIG. 6 can be implemented on the healthcare computer system 2 illustrated in FIG. 2 (it is noted that in the system on FIG. 1, two samples with the same sample ID and time stamp would automatically be given the same anonymised sample ID). The first steps of the method in FIG. 6 are the receipt of a first healthcare data packet 100 (step S611) and the receipt of the second healthcare data packet 100 (step S612), both healthcare data packets 100 being received by the communications module 20. Each of the first and second healthcare data packets 100 contains a sample ID and a timestamp as described above in relation to FIG. 3A. The system, for example the communications module 20, is configured to compare the sample IDs of the two healthcare data packets 100 and also compare the timestamp of the two healthcare data packets 100 (step S612). If the two healthcare data packets have matching sample IDs and matching timestamps, that sample ID and timestamp are provided to the string generation unit 22 and, in parallel or in series with the processing of the communications module 20, one random string is generated (step S615) by the random string generator 21 and provided to the string generation module 22. The string generation module 22 is then configured to generate a shared string for the first healthcare data packet 100 and second healthcare data packet 100 (step S620). The string generated is based on the matching sample ID, the matching timestamp and the shared random string, the processing conducted by the string generation module 22 being substantially the same as that discussed in relation to step S520 of FIG. 5 above. Typically data is received by the communications module in batches, and so the system may identify from a given batch (the batch containing a plurality of healthcare data packets) whether any two or more data packets share a sample identifier.

Having generated the shared string, it is passed from the string generation module 22 to the one-way function module 24. The one-way function module 24 is configured to apply a one-way function to the shared generated string to generated a shared anonymised sample ID (step S630), with the processing conducted by the one-way function module 24 at step S630 being substantially the same as that discussed in relation to step S430 of FIG. 4 above.

Once a shared anonymised sample ID is generated, it is provided to the anonymised data generation module 26. Using the shared anonymised sample ID and the data pertaining to the medical analytical tests performed on the sample in the first and second healthcare data packets 100, the anonymised data generation module 26 generates a first anonymised healthcare data packet including the shared anonymised sample ID and the medical analytical test data contained within the first healthcare data packet 100 and generates a second anonymised healthcare data packet including the shared anonymised sample ID and the medical analytical test data contained within the second healthcare data packet 100 (step S640). Thus, the healthcare computer system 2 can receive first and second healthcare data packets 100 that have a common sample ID and timestamp, and from those healthcare data packets 100, generate two anonymised healthcare data packets that have a shared anonymised sample ID, such that the healthcare data packets can still be associated with each other even once anonymised so that it is not possible to identify the patient that the sample originates from. Generally, the healthcare data packets (anonymised or not) may contain further information relating to the medical analytical tests.

Having generated the first and second anonymised healthcare data packets within the anonymised data generation module 26 (step S640), the first and second anonymised healthcare data packets can be provided to the communications module 20 for transmission to a location outside the LIS 1000 (step S650). The transmission may be to another system within the network for further processing or may be to the server 4 for inclusion in an anonymised healthcare dataset.

Where the timestamp contained within the healthcare data packets 100 contains more granular information than merely the date, the communications module 10 may disregard the more granular information and only consider the date for the purpose of determining if the healthcare data packets have matching timestamps (step S612).

Figure 4:
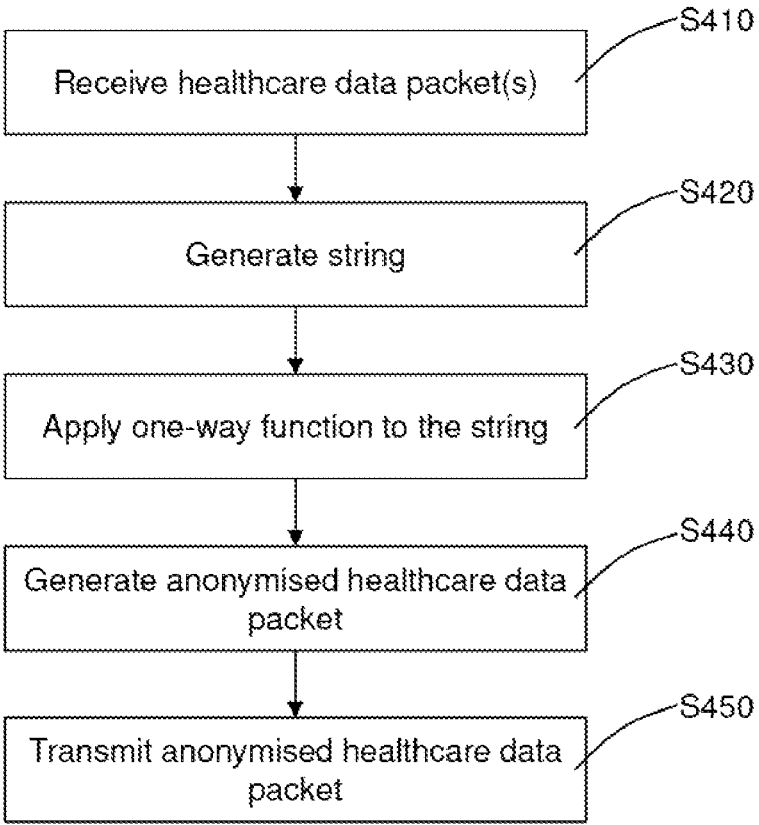
FIG. 4 is a flowchart corresponding to the steps of a computer-implemented method of generating anonymised healthcare data.

If the communications module 20 determines that the first healthcare data packets 100 do not have matching sample IDs and matching timestamps at step S612, the healthcare computer system 2 can proceed to step S420 of FIG. 4 or step S520 of FIG. 5 and continue to generate anonymised healthcare data packets corresponding to the first and second healthcare data packets 100. However, those anonymised healthcare data packets will not have the same anonymised sample ID, because one or more of the sample ID, timestamp and random string on which the string is based will differ between the first healthcare data packet 100 and the second healthcare data packet 100.

The term 'laboratory instrument' as used herein encompasses any apparatus or apparatus component operable to execute one or more processing steps/workflow steps on one or more biological samples and/or one or more reagents. The term 'instrument' covers pre-analytical instruments, post-analytical instruments and also analytical instruments.

The term 'analyzer'/'analytical instrument' as used herein encompasses any apparatus or apparatus component configured to obtain a measurement value. An analyzer is operable to determine via various chemical, biological, physical, optical or other technical procedures a parameter value of the sample or a component thereof. An analyzer may be operable to measure said parameter of the sample or of at least one analyte and return the obtained measurement value. The list of possible analysis results returned by the analyzer comprises, without limitation, concentrations of the analyte in the sample, a digital (yes or no) result indicating the existence of the analyte in the sample (corresponding to a concentration above the detection level), optical parameters, DNA or RNA sequences, data obtained from mass spectrometry of proteins or metabolites and physical or chemical parameters of various types. An analytical instrument may comprise units assisting with the pipetting, dosing, and mixing of samples and/or reagents. The analyzer may comprise a reagent holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. The analyzer may comprise a process and detection system whose workflow is optimized for certain types of analysis. Examples of such analyzers are clinical chemistry analyzers, coagulation chemistry analyzers, immunochemistry analyzers, urine analyzers, nucleic acid analyzers, used to detect the result of chemical or biological reactions or to monitor the progress of chemical or biological reactions.

The term 'pre-analytical instrument' as used herein encompasses any apparatus or apparatus component that is configured to perform one or more pre-analytical workflow steps comprising—but not limited to—centrifugation, resuspension (e.g. by mixing or vortexing), capping, decapping, recapping, sorting, tube type identification, sample quality determination and/or aliquotation steps. Said steps may also comprise adding chemicals or buffers to a sample, concentrating a sample, incubating a sample, and the like.

The term 'post-analytical instrument' as used herein encompasses any apparatus or apparatus component that is configured to perform one or more post-analytical workflow steps comprising—but not limited to—sample unloading, transport, recapping, decapping, temporary storage/buffering, archiving (refrigerated or not), retrieval and/or disposal.

The term 'point-of-care device' as used herein encompasses any analyzer used in a point-of-care environment, such as (but not limited to) blood glucose testing, coagulation testing, blood gas and electrolytes analysis, urinalysis, cardiac markers analysis, hemoglobin diagnostics, infectious disease testing, cholesterol screening or nucleic acid testing NAT. Results may be viewed directly on the POC analyzer/device(s) or may be sent to and displayed in a healthcare information management system.

The term 'healthcare data' as used herein encompasses any data obtained from one or more medical devices through operation of such a device on one or more patients, or one or more samples obtained therefrom.

The term 'connected' as used herein encompasses both direct and indirect communication pathways between two or more elements. A communications pathway may be provided through a physical entity such as a wired connection or may be provided through a non-physical communication system such as a network.

The systems and methods of the above embodiments may be implemented in a computer system (in particular in computer hardware or in computer software) in addition to the structural components and user interactions described.

The term 'computer system' includes the hardware, software and data storage devices for embodying a system or carrying out a method according to the above described embodiments. For example, a computer system may comprise a central processing unit (CPU), input means, output means and data storage. The computer system may have a monitor to provide a visual output display. The data storage may comprise RAM, disk drives or other computer readable media. The computer system may include a plurality of computing devices connected by a network and able to communicate with each other over that network, and in such instances may be referred to as a computer network.

The methods of the above embodiments may be provided as computer programs or as computer program products or computer readable media carrying a computer program which is arranged, when run on a computer, to perform the method(s) described above.

The term 'computer readable media' includes, without limitation, any non-transitory medium or media which can be read and accessed directly by a computer or computer system. The media can include, but are not limited to, magnetic storage media such as floppy discs, hard disc storage media and magnetic tape; optical storage media such as optical discs or CD-ROMs; electrical storage media such as memory, including RAM, ROM and flash memory; and hybrids and combinations of the above such as magnetic/optical storage media.

While the disclosure has been described in conjunction with the exemplary embodiments described above, many equivalent modifications and variations will be apparent to those skilled in the art when given this disclosure. Accordingly, the exemplary embodiments of the disclosure set forth above are considered to be illustrative and not limiting. Various changes to the described embodiments may be made without departing from the spirit and scope of the disclosure.

In particular, although the methods of the above embodiments have been described as being implemented on the systems of the embodiments described, the methods and systems of the present disclosure need not be implemented in conjunction with each other, but can be implemented on alternative systems or using alternative methods respectively.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the disclosure in diverse forms thereof.

While the disclosure has been described in conjunction with the exemplary embodiments described above, many equivalent modifications and variations will be apparent to those skilled in the art when given this disclosure. Accordingly, the exemplary embodiments of the disclosure set forth above are considered to be illustrative and not limiting. Various changes to the described embodiments may be made without departing from the spirit and scope of the disclosure.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example+/−10%.

1. A medical laboratory computer system (1, 2), the medical laboratory computer system (1, 2) comprising:

a communications module (10, 20), configured to receive one or more healthcare data packets (100), each healthcare data packet (100) including:

data pertaining to one or more medical analytical tests performed on a sample;

a sample identifier, identifying the sample; and a timestamp;

a string generation module (12, 22), configured to generate a string based on: the sample identifier and the timestamp;

a one-way function module (14, 24), configured to apply a one-way function to the generated string to generate an anonymised sample identifier; and an anonymised data generation module (16, 26), configured to generate an anonymised healthcare data packet including:

the data pertaining to one or more medical analytical tests, and the anonymised sample identifier.

2. The medical laboratory computer system (1, 2) of clause 1, wherein the computer system (1, 2) further comprises a random string generator (21), configured to generate a random string, and wherein the string generation module (12, 22) is configured to generate the string further based on the random string.

3. The medical laboratory computer system (1, 2) of clause 2, wherein:

the communications module (10, 20) is configured to receive a first healthcare data packet (100) of the one or more healthcare data packets (100) and a second healthcare data packet (100) of the one or more healthcare data packets (100), wherein the first healthcare data packet (100) and the second healthcare data packet (100) include a same sample identifier and a same timestamp;

the random string generator (21) is configured to generate a shared random string for the first and second healthcare data packets (100);

the one-way function module (14, 24) is configured to generate a same anonymised sample identifier for each of the first and second healthcare data packets (100); and the anonymised data generation module (16, 26) is configured to generate a first anonymised healthcare data packet and a second anonymised healthcare data packet, the first and second anonymised healthcare data packets having the same anonymised sample identifier.

4. The medical laboratory computer system (1, 2) of any preceding clause, wherein the string generation module (12, 22) is configured to concatenate the sample identifier and the timestamp.

5. The medical laboratory computer system (1, 2) of any preceding clause, wherein the healthcare data packet (100) further includes a facility identifier, identifying the facility in which the one or more analytical tests were performed, and wherein the string generation module (12, 22) is configured to generate the string further based on the facility identifier.

6. The medical laboratory computer system (1, 2) of any preceding clause, wherein the one-way function module (14, 24) is configured to apply a cryptographic hash function to the string to generate the anonymised sample identifier.

7. The medical laboratory computer system (1, 2) of any preceding clause, wherein the timestamp is indicative of a counting period, the counting period defining a period of time over which sample identifiers are generated and at the end of which the counting period sample identifiers begin to be reused.

8. The medical laboratory computer system (1, 2) of any preceding clause, wherein the communications module (10, 20) is further configured to transmit the anonymised healthcare data packet to a server (4) for inclusion in an anonymised healthcare dataset.

9. The medical laboratory computer system (1, 2) of clause 8, wherein the communications module (10, 20) is configured to group a plurality of anonymised healthcare data packets over a time period, and transmit them in batches to the server (4).

10. The medical laboratory computer system (1, 2) of any preceding clause, wherein the communications module (10, 20) and anonymised data generation module (16, 26) are within a first security area (5) of a network, and the communications module (10, 20) is configured to transmit the anonymised healthcare data packet outside of the first security area (5).

REFERENCE NUMERALS

1,2 medical laboratory computer system
3 network modem

4 server
5 first security area
10, 20 communications module
12, 22 string generation module
14, 24 one-way function module
16, 26 anonymised data generation module
100 healthcare data packets

The invention claimed is:

1. A healthcare computer system, the healthcare computer system comprising:

one or more processors programmed to perform operations comprising:

receiving one or more healthcare data packets, each healthcare data packet including:

data pertaining to one or more medical analytical tests performed on a sample, a sample identifier identifying the sample, and a timestamp consisting of a date;

applying a cryptographic hash function to the sample identifier to generate an encrypted sample identifier;

applying the cryptographic hash function to the timestamp to generate an encrypted timestamp;

generating a random string;

processing the encrypted sample identifier, the random string, and the encrypted timestamp to generate a composite string;

applying the cryptographic hash function to the composite string to generate an anonymised sample identifier; and generating an anonymised healthcare data packet including:

the data pertaining to one or more medical analytical tests, and the anonymised sample identifier.

2. The healthcare computer system of claim 1, wherein the operations further comprise extracting the timestamp from granular time information associated with the healthcare data packet.

3. The healthcare computer system of claim 2, wherein:

the timestamp is indicative of a counting period during which sample identifiers are generated, and a single random string is used with all healthcare data packets within the counting period.

4. The healthcare computer system of claim 1, wherein the operations further comprise:

receiving second one or more healthcare data packets, each of the second one or more healthcare data packets including:

second data pertaining to second one or more medical analytical tests performed on the sample, the sample identifier, and the timestamp, and generating a second anonymised healthcare data packet, the second anonymised healthcare data packet including:

the second data pertaining to second one or more medical analytical tests, and the anonymised sample identifier.

5. The healthcare computer system of claim 1, wherein the healthcare data packet further includes a facility identifier identifying the facility in which the one or more analytical tests were performed, and wherein processing the encrypted sample identifier, the random string, and the encrypted timestamp to generate the composite string comprises concatenating the facility identifier with the encrypted sample identifier, the random string, and the encrypted timestamp.

6. The healthcare computer system of claim 1, wherein:

the one or more healthcare data packets are received as one or more extensible mark-up language (XML) files, and operations further comprise generating an XML file comprising the anonymised healthcare data packet.

7. The healthcare computer system of claim 1, wherein:

the timestamp is indicative of a counting period, the counting period defines a period of time over which sample identifiers are generated, and the sample identifiers are reused after the counting period ends.

8. The healthcare computer system of claim 1, wherein the operations further comprise transmitting the anonymised healthcare data packet to a server for inclusion in an anonymised healthcare dataset.

9. The healthcare computer system of claim 8, wherein the operations further comprise:

grouping a plurality of anonymised healthcare data packets over a time period; and transmitting the plurality of anonymised healthcare data packets in batches to the server.

10. The healthcare computer system of claim 1, wherein the anonymised healthcare data packet is generated security area of a network and transmitted outside of the security area.

11. A computer-implemented method of generating anonymised healthcare data, comprising steps of:

receiving one or more healthcare data packets, each healthcare data packet including:

data pertaining to one or more medical analytical tests performed on a sample, a sample identifier, identifying the sample, and a timestamp consisting of a date;

applying a cryptographic hash function to the sample identifier to generate an encrypted sample identifier;

applying the cryptographic hash function to the timestamp to generate an encrypted timestamp;

generating a random string:

processing the encrypted sample identifier, the random string, and the encrypted timestamp to generate a composite string, applying a cryptographic hash function to the composite string to generate an anonymised sample identifier; and generating an anonymised healthcare data packet, said anonymised healthcare data packet including:

the data pertaining to one or more medical analytical tests, and the anonymised sample identifier.

12. The computer-implemented method of claim 11, wherein the one or more healthcare data packets originate from an in-vitro diagnostics laboratory.

13. The computer-implemented method of claim 11, further comprising extracting the timestamp from granular time information associated with the healthcare data packet.

14. The computer-implemented method of claim 11, wherein the timestamp is indicative of a counting period during which the sample identifier was generated, and wherein the random string is a same random string used with a plurality of healthcare data packets received within the counting period.

15. The computer-implemented method of claim 11, further comprising:

receiving second one or more healthcare data packets, each of the second one or more healthcare data packets including:

second data pertaining to second one or more medical analytical tests performed on the sample, the sample identifier, and the timestamp, and generating a second anonymised healthcare data packet, the second anonymised healthcare data packet including:

the second data pertaining to second one or more medical analytical tests, and the anonymised sample identifier.

16. The computer-implemented method of claim 11, wherein the healthcare data packet further includes a facility identifier identifying the facility in which the one or more medical analytical tests were performed, and wherein the composite string is further based on the facility identifier.

17. The computer-implemented method of claim 11, wherein processing the encrypted sample identifier, the random string, and the encrypted timestamp to generate the composite string comprises concatenating the encrypted sample identifier, the random string, and the encrypted timestamp to generate the composite string.

18. The computer-implemented method of claim 11, further comprising transmitting the anonymised healthcare data packet to a server for inclusion in an anonymised healthcare dataset.

19. The computer-implemented method of claim 11, further comprising transmitting the anonymised healthcare data packet from within a first security area of a network to an area outside of the first security area.

20. A non-transitory computer-readable storage medium, containing machine executable instructions which, when executed on one or more processors, cause the one or more processors to perform the computer-implemented method of claim 11.

* * * * *